United States Patent
Ho

(10) Patent No.: US 10,603,245 B2
(45) Date of Patent: Mar. 31, 2020

(54) SOLUTION BOTTLE

(71) Applicant: Jui-Sheng Ho, Taichung (TW)

(72) Inventor: Jui-Sheng Ho, Taichung (TW)

(*) Notice: Subject to any disclaimer, the term of this patent is extended or adjusted under 35 U.S.C. 154(b) by 658 days.

(21) Appl. No.: 15/362,809

(22) Filed: Nov. 28, 2016

(65) Prior Publication Data

US 2018/0008509 A1  Jan. 11, 2018

(30) Foreign Application Priority Data

Jul. 11, 2016 (TW) .............. 105121706 A

(51) Int. Cl.
| | | |
|---|---|---|
| *A61H 23/02* | (2006.01) | |
| *A61M 11/00* | (2006.01) | |
| *B65D 83/20* | (2006.01) | |
| *B65D 83/28* | (2006.01) | |
| *B65D 83/38* | (2006.01) | |

(52) U.S. Cl.
CPC ............ *A61H 23/02* (2013.01); *A61M 11/00* (2013.01); *B65D 83/207* (2013.01); *B65D 83/285* (2013.01); *B65D 83/384* (2013.01); *A61H 2201/105* (2013.01); *A61H 2201/1215* (2013.01)

(58) Field of Classification Search
CPC ............ B65D 83/0033; B65D 83/285; B65D 83/207; B65D 83/38; B65D 83/384; B65D 83/386; A61H 23/006; A61H 23/02
See application file for complete search history.

(56) References Cited

U.S. PATENT DOCUMENTS

| | | | | |
|---|---|---|---|---|
| 8,591,133 B2* | 11/2013 | Ho | ............... | A45D 34/041 |
| | | | | 401/209 |
| 2007/0125113 A1* | 6/2007 | Habatjou | ............ | A45D 34/041 |
| | | | | 62/293 |
| 2011/0091264 A1* | 4/2011 | Zhang | .................. | A45D 34/04 |
| | | | | 401/139 |
| 2013/0256338 A1* | 10/2013 | Moreau | ............. | B05B 11/0029 |
| | | | | 222/153.14 |
| 2013/0333718 A1* | 12/2013 | Kim | ..................... | A45D 33/36 |
| | | | | 132/293 |
| 2014/0231464 A1* | 8/2014 | Cho | ................... | B05B 11/3004 |
| | | | | 222/321.8 |
| 2017/0232243 A1* | 8/2017 | Herweijer | ........... | A45D 34/041 |
| | | | | 604/290 |

* cited by examiner

*Primary Examiner* — LaToya M Louis

(57) ABSTRACT

A solution bottle contains: a body and an applying head. The body includes a holder, a first sleeve, and a second sleeve. The holder has an accommodation chamber configured to accommodate a spray can, the first sleeve is secured on a top of the holder, and the second sleeve is connected with an inner wall of the first sleeve. The second sleeve has a connection hole arranged on a bottom thereof and fitting with the spray can, and the second sleeve has a receiving groove configured to house the applying head and communicating with the fitting hole. Thereby, the solution bottle is capable of massaging and applying the solution (such as medicine agent or cosmetics) on the user's body.

3 Claims, 9 Drawing Sheets

SOLUTION BOTTLE

BACKGROUND OF THE INVENTION

Field of the Invention

The present invention relates to a solution bottle which is capable of massaging and applying solution (such as medicine agent or cosmetics) on user's body.

Description of the Prior Art

A conventional solution bottle is used to pour solution on user's body, but it cannot be employed to massage the user.

A solution bottle is disclosed in TW M396042 and contains a body, a pump cylinder, a rolling holder. The body has a thread section formed on an outer wall of a top thereof. The pump cylinder is screwed with the thread section of the body and has an accommodation chamber defined in a top thereof, and the pump cylinder also has a tube extending upwardly from the accommodation chamber. The rolling holder has a through orifice configured to accommodate the tube, a holding room arranged on an outlet section thereof, a limitation seat formed on an opening of the outlet section, a rolling ball, and a cap. However, the solution bottle does not have a spray can which is replaceable.

The present invention has arisen to mitigate and/or obviate the afore-described disadvantages.

SUMMARY OF THE INVENTION

The primary objective of the present invention is to provide a solution bottle which is capable of massaging and applying the solution (such as medicine agent or cosmetics) on user's body.

To obtain the above objectives, a solution bottle provided by the present invention contains: a body and an applying head.

The body includes a holder, a first sleeve, and a second sleeve, wherein the holder has an accommodation chamber configured to accommodate a spray can, the first sleeve is secured on a top of the holder, and the second sleeve is connected with an inner wall of the first sleeve, wherein the second sleeve has a connection hole arranged on a bottom thereof and fitting with the spray can, and the second sleeve has a receiving groove configured to house the applying head and communicating with the fitting hole.

The second sleeve has a first locking rib arranged around an outer wall thereof, and the first sleeve has a first trench defined around an inner wall thereof.

The applying head includes a first seat, a second seat, a vibrator, a conductive ring, a metal disc, and a press disc; the first seat is fitted with the second seat, and the second seat expands and retracts relative to the first seat; the vibrator, the conductive ring, the metal disc, and the press disc are housed in the first seat and the second seat; the first seat has an electric cell electrically connected with the metal disc, and the conductive ring is electrically connected with the vibrator, wherein the metal disc has a gap parallelly corresponding to the conductive ring, the press disc is mounted between the metal disc and the second seat, and the press disc has a tab configured to press the metal disc and to contact with the conductive ring.

The first seat has a rotary cap, a first loop, a second loop, a holding disc, and a bottom lid; the first loop is fitted on an upper end of an outer wall of the second loop, and the second loop accommodates the electric cell and the vibrator, the rotary cap is covered on the first loop, wherein the rotary cap, the first loop, and the second loop define a housing space for accommodating the electric cell, and the rotary cap is removed from the first loop so as to replace the electric cell. The holding disc is located beneath the second loop, the conductive ring is mounted on a top of the holding disc, and the metal disc is fixed on a bottom of the holding disc, wherein the holding disc has a through orifice so that the metal disc touches the conductive ring via the through orifice. The bottom lid is located beneath the holding disc, the press disc is defined between the bottom lid and the second seat, the bottom lid has an aperture configured to insert the tab of the press disc, and the metal disc is clamped between the bottom lid and the holding disc. The second loop has a second locking rib arranged around an outer wall thereof, and the second seat has a second trench defined around an inner wall thereof.

DETAILED DESCRIPTION OF THE PREFERRED EMBODIMENTS

Figure 1:
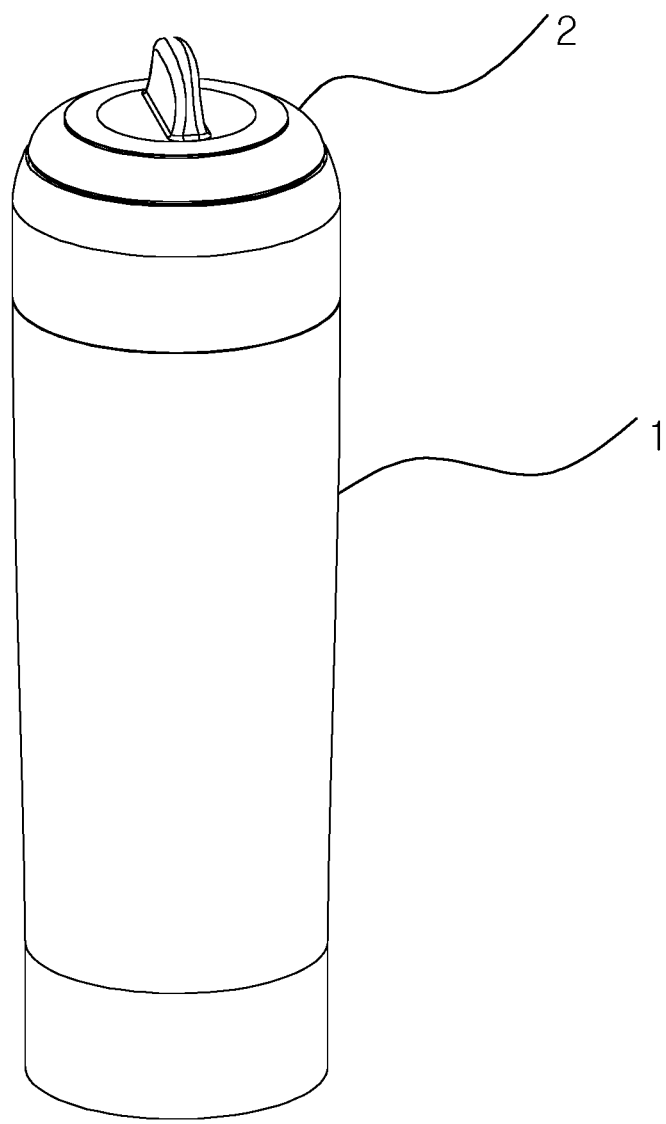
FIG. 1 is a perspective view showing the assembly of a solution bottle according to a preferred embodiment of the present invention.
Figure 2:
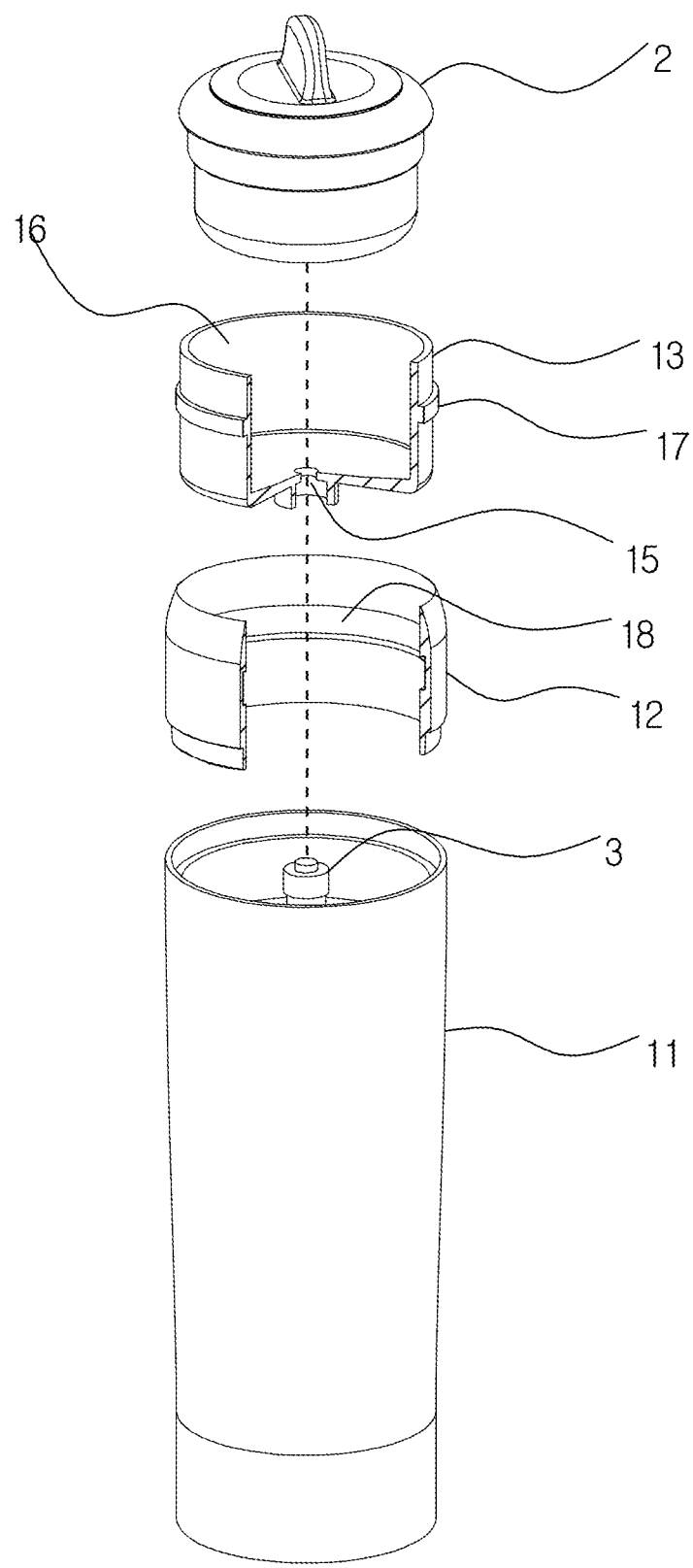
FIG. 2 is a perspective view showing the exploded components of the solution bottle according to the preferred embodiment of the present invention.
Figure 3:
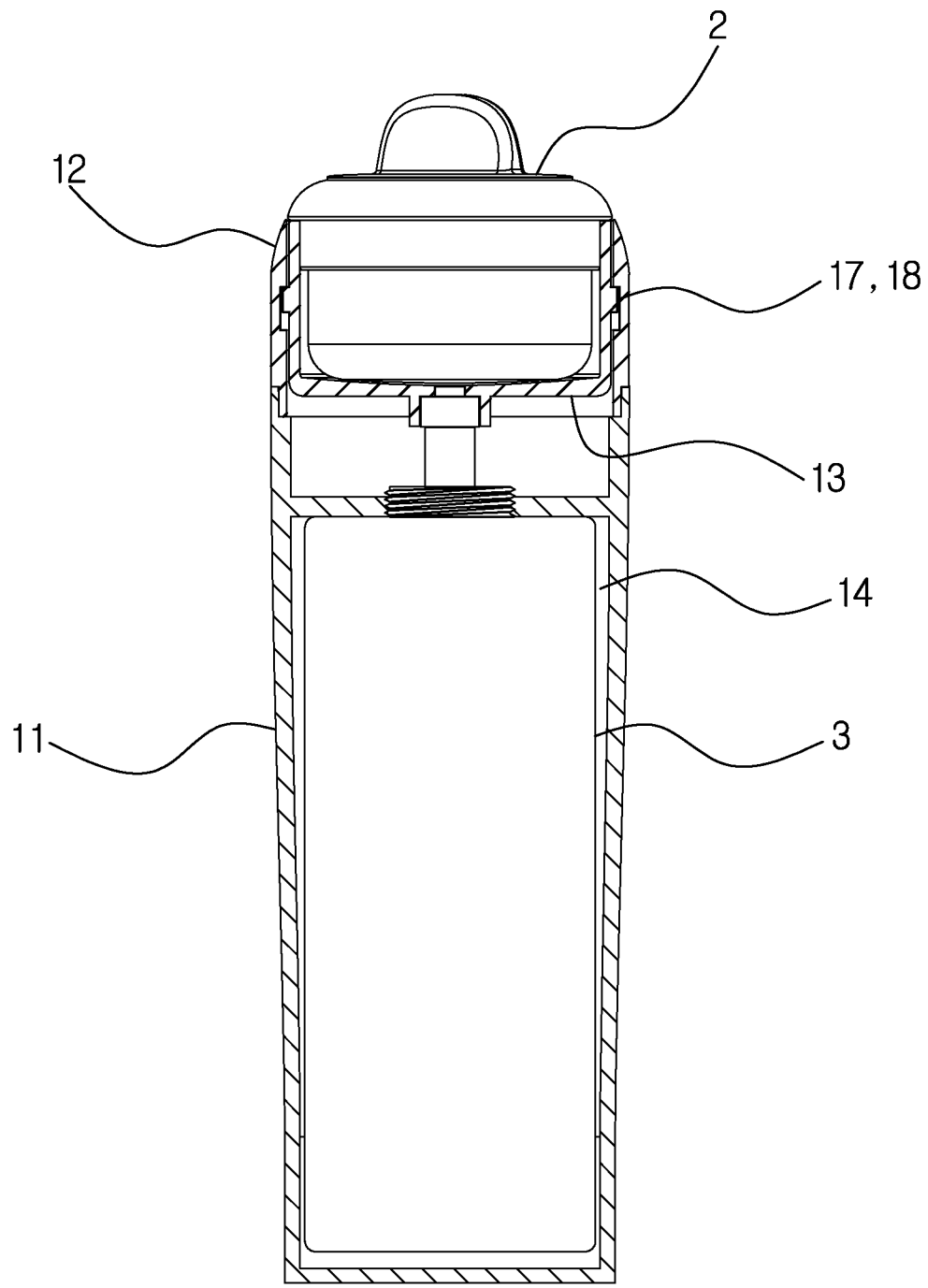
FIG. 3 is a cross sectional view showing the assembly of the solution bottle according to the preferred embodiment of the present invention.
Figure 4:
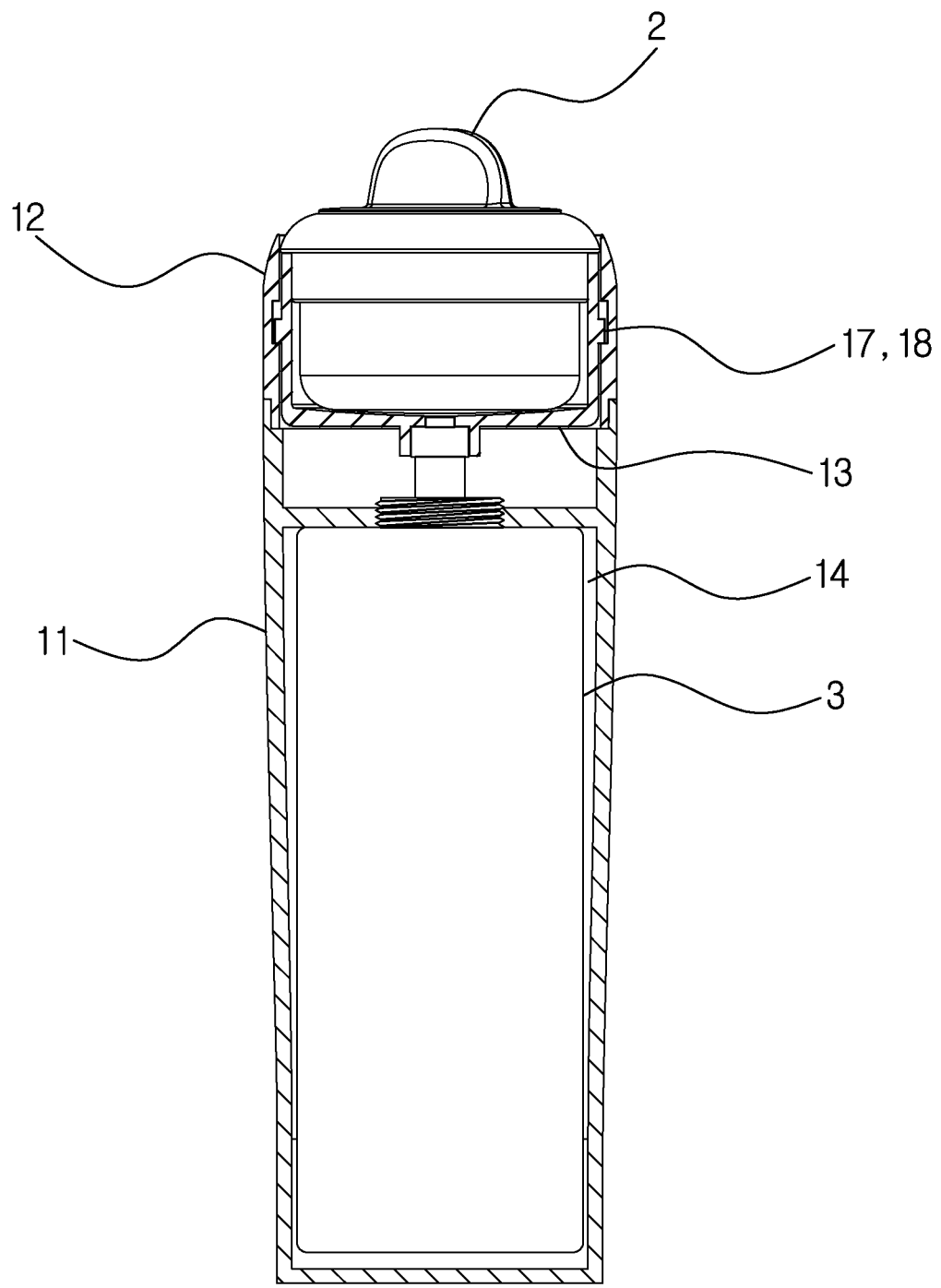
FIG. 4 is a cross sectional view showing the operation of the solution bottle according to the preferred embodiment of the present invention.

With reference to FIGS. 1 to 4, a solution bottle according to a preferred embodiment of the present invention comprises: a body 1 and an applying head 2.

The body 1 includes a holder 11, a first sleeve 12, and a second sleeve 13, wherein the holder 11 has an accommodation chamber 14 configured to accommodate a spray can 3. In this embodiment, the holder 11 is close. Alternatively, the holder 11 is open and the spray can 3 is replaceable. The first sleeve 12 is secured on a top of the holder 11, and the second sleeve 13 is connected with an inner wall of the first sleeve 12, wherein the second sleeve 13 has a connection hole 15 arranged on a bottom thereof and fitting with the spray can 3, and the second sleeve 13 has a receiving groove 16 configured to house the applying head 2 and communicating with the fitting hole 15.

After pressing the applying head 2, the second sleeve 13 moves relative to the first sleeve 12 so as to press the spray can 3, and solution is fed into the receiving groove 16 from the connection hole 15, hence the applying head 2 dips the solution, and user applies the solution on his/her body.

The second sleeve 13 has a first locking rib 17 arranged around an outer wall thereof, and the first sleeve 12 has a first trench 18 defined around an inner wall thereof, hence the first locking rib 17 engages with the first trench 18 so that the second sleeve 13 moves relative to the first sleeve 12.

Figure 5:
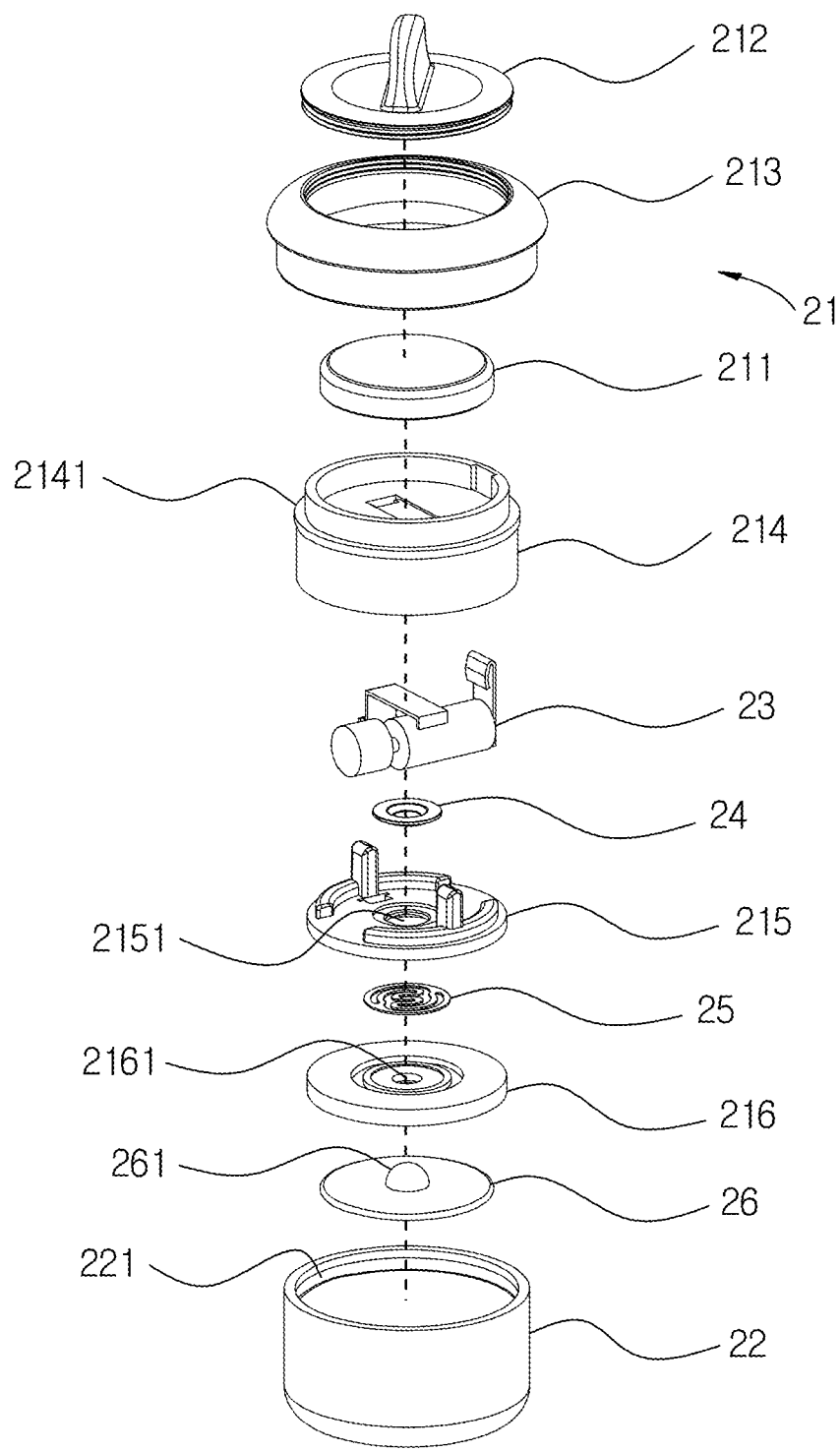
FIG. 5 is a perspective view showing the exploded components of a part of the solution bottle according to the preferred embodiment of the present invention.
Figure 6:
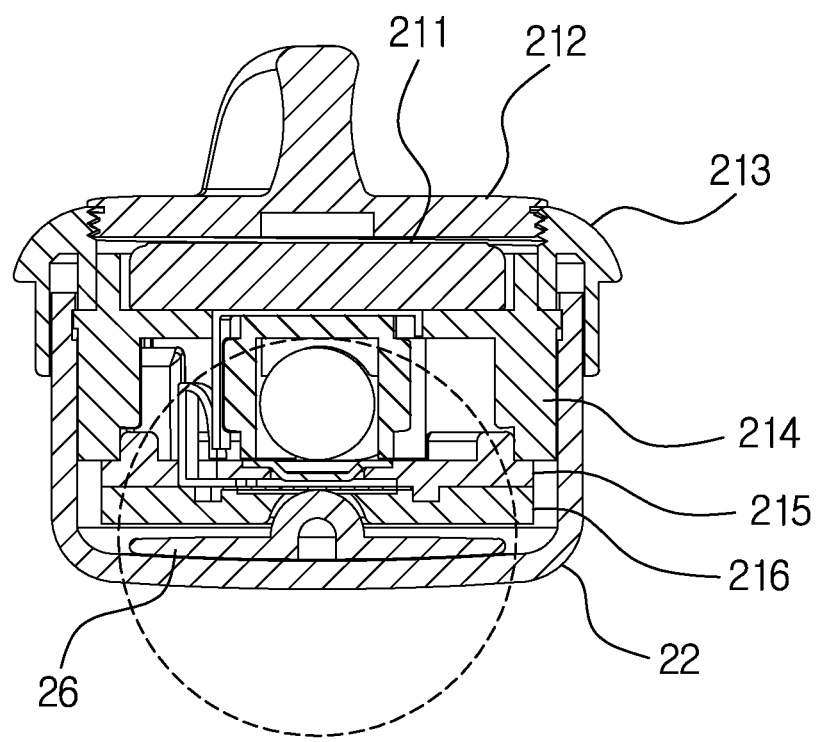
FIG. 6 is a cross sectional view showing the operation of a part of the solution bottle according to the preferred embodiment of the present invention.
Figure 7:
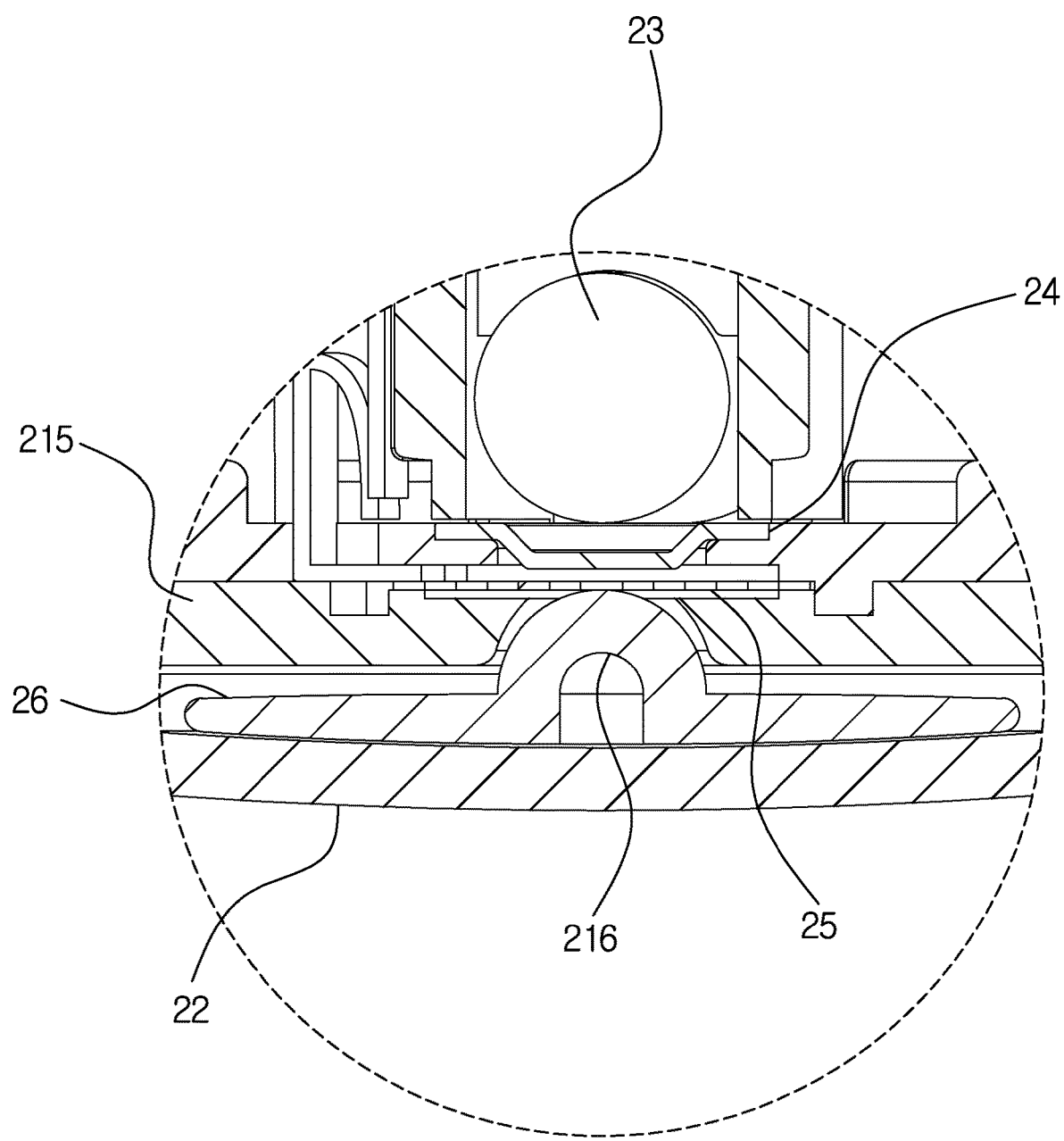
FIG. 7 is an amplified cross sectional view of FIG. 6.
Figure 8:
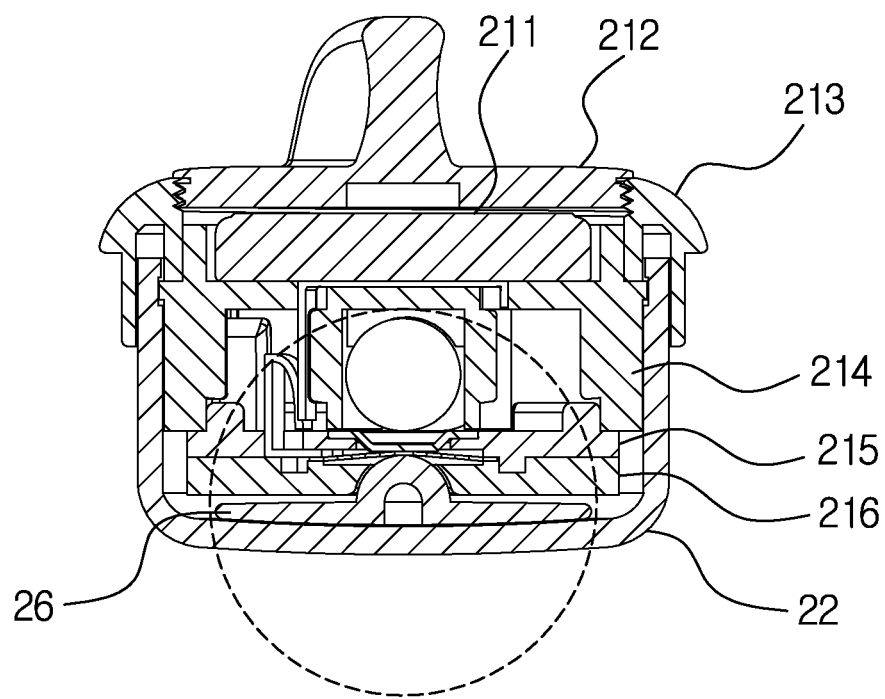
FIG. 8 is another cross sectional view showing the operation of a part of the solution bottle according to the preferred embodiment of the present invention.
Figure 9:
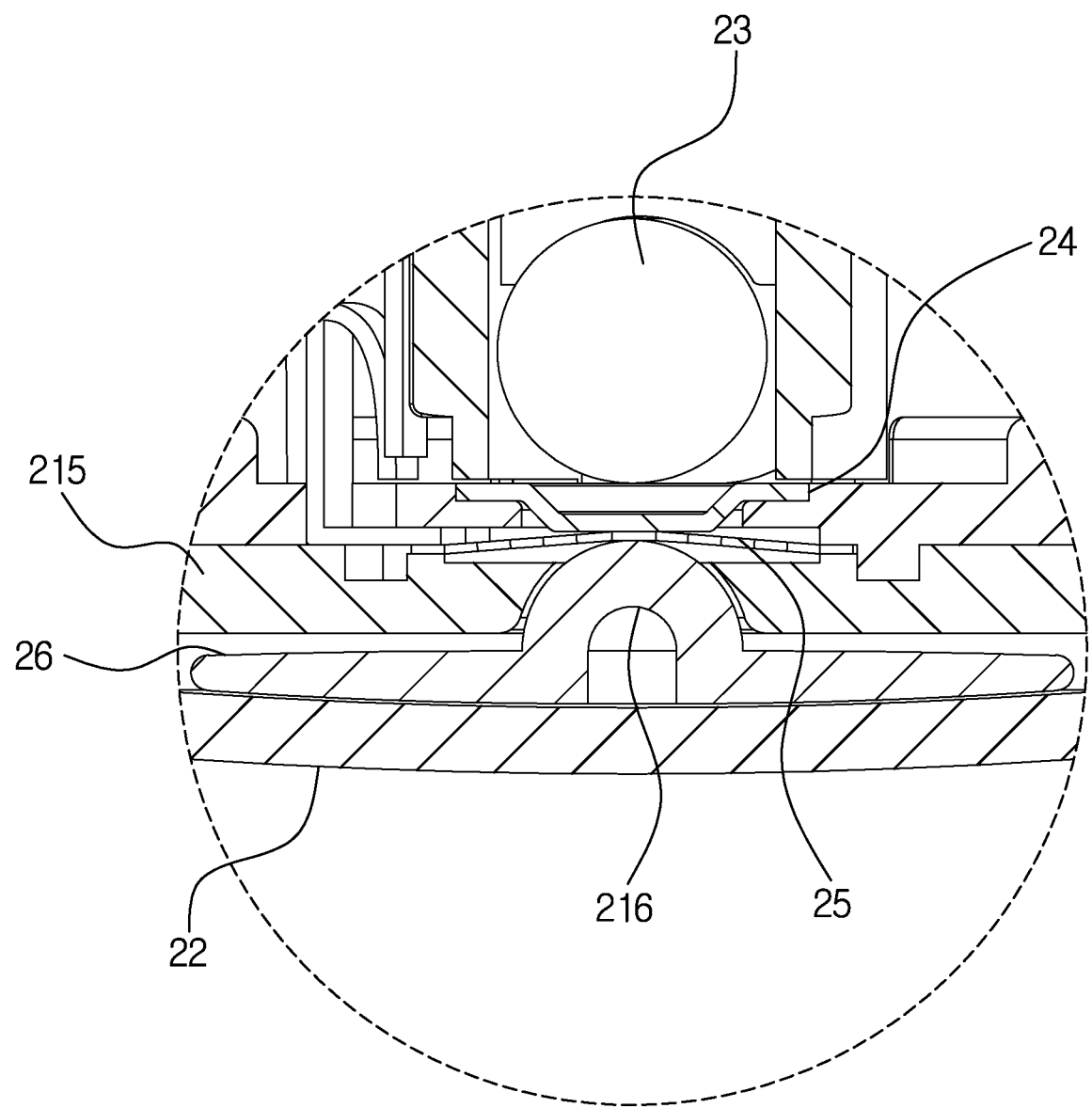
FIG. 9 is an amplified cross sectional view of FIG. 8.

Referring to FIG. 5, the applying head 2 includes a first seat 21, a second seat 22, a vibrator 23, a conductive ring 24, a metal disc 25, and a press disc 26. The first seat 21 is fitted with the second seat 22, and the second seat 22 expands and retracts relative to the first seat 21. The vibrator 23, the conductive ring 24, the metal disc 25, and the press disc 26 are housed in the first seat 21 and the second seat 22, the first seat 21 has an electric cell 211 electrically connected with the metal disc 25, and the conductive ring 24 is electrically connected with the vibrator 23, wherein the metal disc 25 has a gap parallelly corresponding to the conductive ring 24, the press disc 26 is mounted between the metal disc 25 and the second seat 22, and the press disc 26 has a tab 261 configured to press the metal disc 25 and to contact with the conductive ring 24.

As shown in FIGS. 6 to 9, the second seat 22 retracts relative to the first seat 21 so as to drive the tab 261 of the press disc 26 to force the metal disc 25, and the metal disc 25 deforms to touch the conductive ring 24 so that the electric cell 211 electrically conducts with the vibrator 23, and the vibrator 23 vibrates so that the solution bottle massages and applies the solution to the user.

As illustrated in FIG. 5, the first seat 21 has a rotary cap 212, a first loop 213, a second loop 214, a holding disc 215, and a bottom lid 216. The first loop 213 is fitted on an upper end of an outer wall of the second loop 214, and the second loop 214 accommodates the electric cell 211 and the vibrator 23, the rotary cap 212 is covered on the first loop 213, wherein the rotary cap 212, the first loop 213, and the second loop 214 define a housing space for accommodating the electric cell 211, and the rotary cap 212 is removed from the first loop 213 so as to replace the electric cell 211.

The holding disc 215 is located beneath the second loop 214, the conductive ring 24 is mounted on a top of the holding disc 215, and the metal disc 25 is fixed on a bottom of the holding disc 215, wherein the holding disc 215 has a through orifice 2151 so that the metal disc 25 touches the conductive ring 24 via the through orifice 2151. The holding disc 215 separates the conductive ring 24 from the metal disc 25 so that a gap forms between the conductive ring 24 and the metal disc 25, and the vibrator 23 and the conductive ring 24 are fixed in the second loop 214, wherein the bottom lid 216 is located beneath the holding disc 215, the press disc 26 is defined between the bottom lid 216 and the second seat 22, the bottom lid 216 has an aperture 2161 configured to insert the tab 261 of the press disc 26, and the metal disc 25 is clamped between the bottom lid 216 and the holding disc 215. The second loop 214 has a second locking rib 2141 arranged around an outer wall thereof, and the second seat 22 has a second trench 221 defined around an inner wall thereof, hence the first locking rib 17 engages with the first trench 18 so that the second seat 22 expands and extracts relative to the first seat 21 by way of the second trench 221 and the second locking rib 2141.

Thereby, the solution bottle is capable of massaging and applying the solution (such as medicine agent or cosmetics) on the user's body.

While the preferred embodiments of the invention have been set forth for the purpose of disclosure, modifications of the disclosed embodiments of the invention and other embodiments thereof may occur to those skilled in the art. Accordingly, the appended claims are intended to cover all embodiments which do not depart from the spirit and scope of the invention.

What is claimed is:

1. A solution bottle comprising: a body and an applying head;
   wherein the body includes a holder, a first sleeve, and a second sleeve, wherein the holder has an accommodation chamber configured to accommodate a spray can, the first sleeve is secured on a top of the holder, and the second sleeve is connected with an inner wall of the first sleeve, wherein the second sleeve has a connection hole arranged on a bottom thereof and fitting with the spray can, and the second sleeve has a receiving groove configured to house the applying head and communicating with the fitting hole,
   wherein the applying head includes a first seat, a second seat, a vibrator, a conductive ring, a metal disc, and a press disc; the first seat is fitted with the second seat, and the second seat expands and retracts relative to the first seat; the vibrator, the conductive ring, the metal disc, and the press disc are housed in the first seat and the second seat; the first seat has an electric cell electrically connected with the metal disc, and the conductive ring is electrically connected with the vibrator, wherein the metal disc has a gap parallelly corresponding to the conductive ring, the press disc is mounted between the metal disc and the second seat, and the press disc has a tab configured to press the metal disc and to contact with the conductive ring.

2. The solution bottle as claimed in claim 1, wherein the second sleeve has a first locking rib arranged around an outer wall thereof, and the first sleeve has a first trench defined around an inner wall thereof.

3. The solution bottle as claimed in claim 1, wherein the first seat has a rotary cap, a first loop, a second loop, a holding disc, and a bottom lid; the first loop is fitted on an upper end of an outer wall of the second loop, and the second loop accommodates the electric cell and the vibrator, the rotary cap is covered on the first loop, wherein the rotary cap, the first loop, and the second loop define a housing space for accommodating the electric cell, and the rotary cap is removed from the first loop so as to replace the electric cell; the holding disc is located beneath the second loop, the conductive ring is mounted on a top of the holding disc, and the metal disc is fixed on a bottom of the holding disc, wherein the holding disc has a through orifice so that the metal disc touches the conductive ring via the through orifice; wherein the bottom lid is located beneath the holding disc, the press disc is defined between the bottom lid and the second seat, the bottom lid has an aperture configured to insert the tab of the press disc, and the metal disc is clamped between the bottom lid and the holding disc; the second loop has a second locking rib arranged around an outer wall thereof, and the second seat has a second trench defined around an inner wall thereof.

* * * * *